(12) United States Patent
Karst et al.

(10) Patent No.: US 8,936,884 B2
(45) Date of Patent: Jan. 20, 2015

(54) DEVICE AND METHOD FOR CONTROLLING THE HUMIDIFICATION OF A FUEL CELL

(75) Inventors: Nicolas Karst, Folkling (FR); Vincent Faucheux, Lans en Vercors (FR)

(73) Assignees: STMicroelectronics (Tours) SAS, Tours (FR); Commissariat a l'Energie Atomique et aux Energies Alternatives, Paris (FR)

( * ) Notice: Subject to any disclaimer, the term of this patent is extended or adjusted under 35 U.S.C. 154(b) by 1395 days.

(21) Appl. No.: 12/624,904

(22) Filed: Nov. 24, 2009

(65) Prior Publication Data

US 2010/0130265 A1 May 27, 2010

(30) Foreign Application Priority Data

Nov. 26, 2008 (FR) .................................... 08 58031

(51) Int. Cl.
| | |
|---|---|
| H01M 8/06 | (2006.01) |
| H01M 8/00 | (2006.01) |
| H01M 8/04 | (2006.01) |
| H01M 8/24 | (2006.01) |
| G01N 19/10 | (2006.01) |
| H01M 8/02 | (2006.01) |
| H01M 8/10 | (2006.01) |

(52) U.S. Cl.
CPC ...... *H01M 8/04089* (2013.01); *H01M 8/04223* (2013.01); *H01M 8/04291* (2013.01); *H01M 8/04835* (2013.01); *H01M 8/2475* (2013.01); *G01N 19/10* (2013.01); *H01M 8/0291* (2013.01); *H01M 8/04126* (2013.01); *H01M 8/1097* (2013.01); *H01M 2250/30* (2013.01); *Y02E 60/50* (2013.01); *Y02B 90/18* (2013.01)

USPC ............................................ 429/413; 429/400

(58) Field of Classification Search
None
See application file for complete search history.

(56) References Cited

U.S. PATENT DOCUMENTS

| | | | |
|---|---|---|---|
| 6,376,110 B1* | 4/2002 | Koschany | 429/413 |
| 6,497,971 B1 | 12/2002 | Reiser | |
| 2001/0012575 A1* | 8/2001 | Katagiri et al. | 429/22 |
| 2005/0260466 A1* | 11/2005 | Kobayashi et al. | 429/13 |
| 2006/0147766 A1* | 7/2006 | Wang et al. | 429/19 |
| 2008/0057367 A1 | 3/2008 | Nakakubo | |
| 2008/0226965 A1* | 9/2008 | Curello et al. | 429/34 |

FOREIGN PATENT DOCUMENTS

| | | |
|---|---|---|
| DE | 2006041961 A1 | 3/2008 |
| JP | 2005116185 A | 4/2005 |

OTHER PUBLICATIONS

French Search Report dated Jul. 23, 2009 from corresponding French Application No. 08/58031 filed on Nov. 26, 2008.

* cited by examiner

*Primary Examiner* — Barbara Gilliam
*Assistant Examiner* — Adam A Arciero
(74) *Attorney, Agent, or Firm* — Gardere Wynne Sewell LLP

(57) ABSTRACT

An oxygen/hydrogen fuel cell including a package having, on the side of the cell intended to be exposed to air, an enclosure provided with a mobile cap; an element made of a material which deforms according to the humidity ratio in the package; circuitry for controlling the opening and the closing of the mobile cap; and a switch which opens and closes according to the deformation of said material, said switch being associated with control means.

7 Claims, 4 Drawing Sheets

DEVICE AND METHOD FOR CONTROLLING THE HUMIDIFICATION OF A FUEL CELL

CROSS REFERENCE TO RELATED APPLICATIONS

This application claims the priority benefit of French patent application number 08/58031, filed on Nov. 26, 2008, entitled "DEVICE AND METHOD FOR CONTROLLING THE HUMIDIFICATION OF A FUEL CELL," which is hereby incorporated by reference to the maximum extent allowable by law.

BACKGROUND OF THE INVENTION

1. Field of the Invention

The present invention relates to miniature fuel cells and, more specifically, to a device and a method for controlling the humidification of the electrolyte of a fuel cell.

2. Discussion of the Related Art

Hydrogen-oxygen fuel cells having their upper surface forming the cathode of the cell exposed to a hydrogen source are here considered. In such a cell, an electrolyte is sandwiched between the anode and the cathode. On the anode side, an oxidation reaction transforms the oxygen into H+ ions which cross the electrolyte. On the cathode side, the H+ ions having crossed the electrolyte react with the air oxygen to form water. The circulation of the H+ ions (and of complementarily-formed electrons) ensure the cell operation.

The electrolyte is generally formed of a polymer membrane, for example, made of Nafion (trademark of DuPont Corporation). The conductivity to H+ ions of such electrolytes is substantially constant if the humidity ratio of the electrolyte is within a range of values, but strongly decreases if the humidity ratio of the electrolyte falls below this range.

Once the fuel cell has started, the water generated at the cathode ensures that the humidity ratio of the cell remains sufficient. However, for example, when the fuel cell has not been used for a long time and has been kept in a dry and possibly hot atmosphere, the material forming the electrolyte may dry out. In this case, the fuel cell will not start or only weakly so.

FIG. 1 is a curve illustrating the starting problems of an air-breathing fuel cell having its electrolyte in a dried out state. At an initial time when the cell is supplied with hydrogen, it delivers a current density approximately equal to 0.02 A/cm−2. The current flow contributes to heating the cell and the water generated at the cathode evaporates quickly. Thus, the fuel cell electrolyte further dries out, which decreases the current density delivered by the cell down to a value smaller than 0.01 A/cm−2 ten minutes after starting. The current density in the fuel cell thus does not reach the desired nominal values (on the order of from 0.7 to 0.9 A/cm−2).

To solve this problem, it has been provided in prior art (see for example patent application WO 2006/012953 or U.S. Pat. No. 6,830,841) to control the humidification of the electrolyte of a fuel cell by adjusting the humidity ratio of the gases supplied to the cell. Such systems for modifying the humidity ratio of the gases supplied to the cell are relatively complex and are not adapted to simple fuel cells. Such systems are also not adapted to miniature fuel cells, especially fuel cells intended to power small electronic devices such as cell phones.

To maintain the humidity of a fuel cell, it has also been provided to cover the cell cathode surface with a cap which is closed during periods when the cell is not used (see US-A1-2007/218338, JP-A-2005/032517, US-A1-2007/228740). This solution is ineffective in the case where the cell is not used for long periods, since it dries out after some time, however well protected it may be.

SUMMARY OF THE INVENTION

An object of at least one embodiment of the present invention is to provide a device comprising a fuel cell capable of starting when its electrolyte is in a dried out state.

More specifically, an object of at least one embodiment of the present invention is to provide a low-bulk device.

Another object of at least one embodiment of the present invention is to provide a self-sufficient device.

Another object of at least on embodiment of the present invention is to provide a device adapted to a cell phone.

Thus, an embodiment of the present invention provides an oxygen/hydrogen fuel cell comprising: a package comprising, on the side of the cell intended to be exposed to air, an enclosure provided with a mobile cap; an element made of material which deforms according to the humidity ratio in the package; means for controlling the opening and the closing of the mobile cap; and a switch which opens and closes according to the deformation of said material, said switch being associated with control means.

According to an embodiment of the present invention, the fuel cell comprises a layer forming an electrolyte and the material deforming according to the humidity ratio in the package is identical to the material forming the electrolyte.

According to an embodiment of the present invention, the switch and the control means are series-connected between two electrodes of the fuel cell.

According to an embodiment of the present invention, the control means comprise a motor.

According to an embodiment of the present invention, a capacitor is connected in parallel on the motor.

According to an embodiment of the present invention, the fuel cell comprises at least one second switch sensitive to the humidity ratio in the package and associated with control means.

An embodiment of the present invention further provides a method for starting an oxygen/hydrogen fuel cell formed in a package, comprising a step of closing of a mobile cap of the package, on the side of the cell intended to be exposed to oxygen, followed by a step of opening of the cap when the humidity ratio in the cell package reaches a predetermined threshold, the energy produced by the cell being used to open the cap.

An embodiment of the present invention further provides a cell phone comprising a fuel cell such as described hereabove.

The foregoing objects, features, and advantages of the present invention will be discussed in detail in the following non-limiting description of specific embodiments in connection with the accompanying drawings.

DETAILED DESCRIPTION

Figure 1:
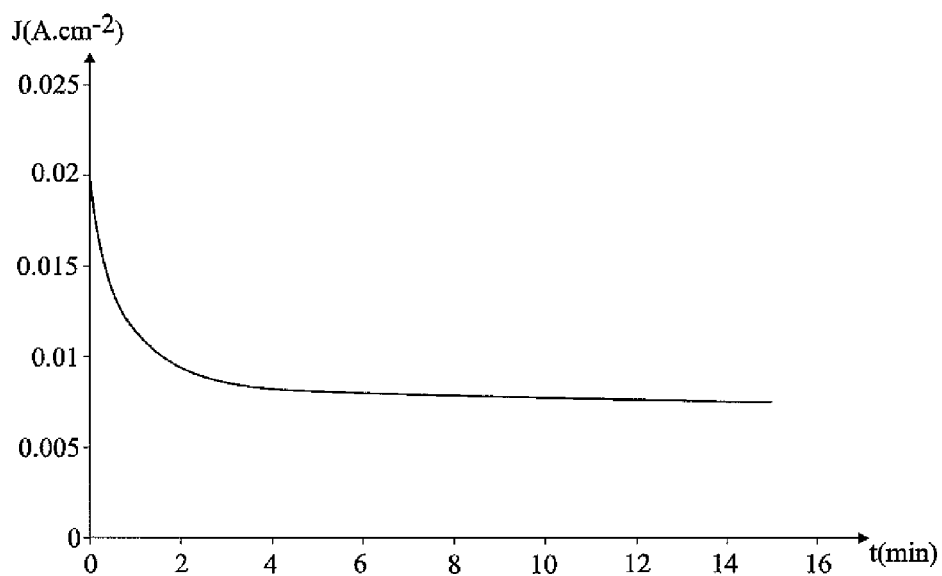
FIG. 1, previously described, is a curve illustrating the starting problems of a fuel cell having its electrolyte in a dried out state.

For clarity, the same elements have been designated with the same reference numerals in the different drawings and, further, as usual, the various drawings are not to scale.

Figure 2:
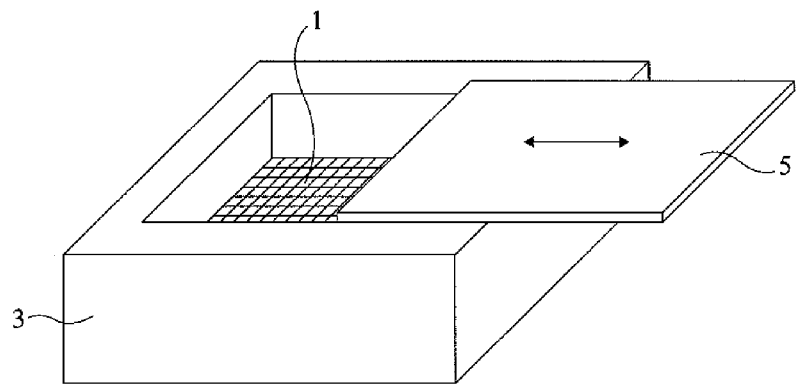
FIG. 2 illustrates a fuel cell package according to the present invention.

FIG. 2 illustrates an embodiment of a fuel cell package.

The upper surface, on the cathode side, of one or several fuel cells 1 is arranged in an enclosure or package 3. Package 3 is provided with a mobile cap 5, for example, a sliding cap. Mobile cap 5 may be positioned to open or close enclosure 3. A hydrogen tank, not shown in FIG. 2, may be attached to the lower part of package 3. To control the humidity in the enclosure, mobile cap 5 will be appropriately opened or closed.

The structure of the package of FIG. 2 is an example only and many different mobile cap structures may be used. For example, the mobile cap may be formed of lugs, or again of interlaced grids.

Figure 3:
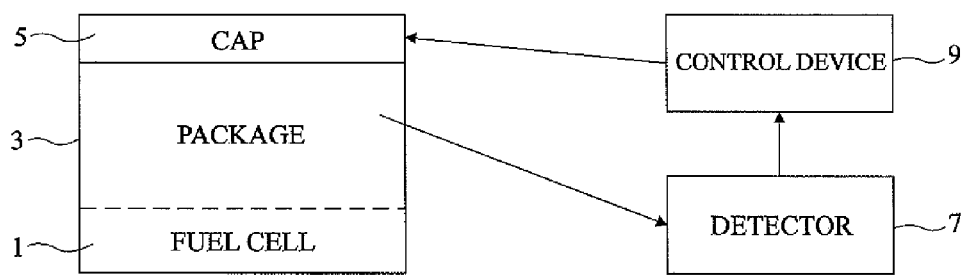
FIG. 3 is a block diagram of a humidity control device according to an embodiment of the present invention.

FIG. 3 is a block diagram of an embodiment of a device for controlling the humidity of a fuel cell. Fuel cell(s) 1, package 3 and its mobile cap 5 have been schematically shown. The device further comprises a detector 7 of the humidity ratio in enclosure 3 and a control device 9 which receives information from detector 7 and which controls the displacement of mobile cap 5.

The device operates as follows. To start the fuel cell, the mobile cap is placed in closed position. It should be noted that "closed cap" is here used to designate a cap having its opening rate ranging between 0 and 5%. The fuel cell is then started, that is, it is supplied with hydrogen. If the electrolyte of the fuel cell is dry, the fuel cell delivers a relatively low current and releases, on its cathode side, a few water molecules which evaporate in the closed package. Thus, the relative humidity ratio in closed enclosure 3 increases and the electrolyte of the fuel cell hydrates. When the relative humidity ratio in the enclosure reaches a predetermined threshold, for example, greater than 80%, detector 7 provides information to actuator 9, which triggers the opening of mobile cap 5 and puts the cathode of the fuel cell in contact with air. Enclosure 3 will be provided with a volume sufficient for the electrolyte of the fuel cell to hydrate properly, while avoiding the cell flooding (which occurs when water covers the cathode and said cell is no longer in contact with air).

Figure 4:
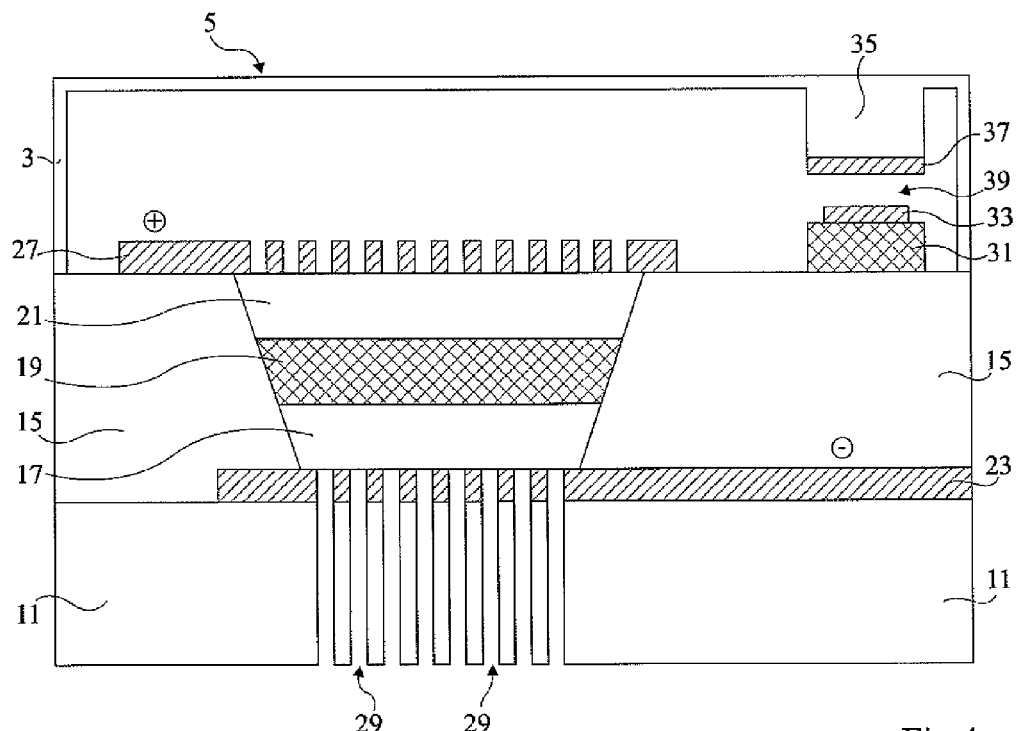
FIGS. 4 to 6 illustrate various embodiments of humidity control devices.

FIG. 4 illustrates a first embodiment of a humidity control device. To make things clearer, a specific example of a fuel cell has also be shown.

The fuel cell is formed on a wafer 11 coated with a thick insulating layer 15. Wafer 11 may be made of silicon, ceramic, graphite, silicon carbide, polymer, glass . . . . In an opening of insulating layer 15 are located the active elements of the cell, that is, a first catalyst layer 17, an electrolyte 19, and a second catalyst layer 21. A lower electrode 23, placed on wafer 11, is in contact with lower catalyst layer 17. An upper electrode 27 is in contact with upper catalyst layer 21. Electrodes 23 and 27 are provided with openings, and channels 29 are formed in wafer 11, opposite to the openings in lower surface metallization 23. Lower electrode 23 and upper electrode 27 respectively form an anode collector and a cathode collector.

Electrolyte 19 may be made of a polymer such as Nafion in solid form and catalyst layers 17 and 21 for example are carbon- and platinum-based layers. In known fashion, with such a structure, a positive potential is obtained on cathode collector 27 (on the oxygen side) and a negative potential is obtained on anode collector 23 (on the hydrogen side). This is an example of embodiment only. Various types of fuel cells are known in the art.

Hydrogen is injected on the lower surface side into channels 29. Package 3 of the fuel cell comprising mobile cap 5 is located on the side of cathode collector 21. In FIG. 4, mobile cap 5 is closed and the structure allowing it to open and close is not shown.

A pad 31 made of a material deforming according to the humidity ratio in the package is arranged on insulating layer 15. As an example, this material may be the same as that forming electrolyte 19, for example, Nafion which expands when the humidity ratio increases. A first metal terminal 33 extends on pad 31. The upper portion of the fuel cell package comprises a vertical extension 35, opposite to terminal 33, on which a second metal terminal 37 extends.

When electrolyte 19 of the fuel cell is in a dried out state, the material of pad 31 is also dry, and metal terminals 33 and 37 do not touch. When the humidity ratio in the package increases, the volume of pad 31 increases, whereby terminals 33 and 37 end up touching each other. Thus, a switch 39 formed of terminals 33 and 37 is closed, and the corresponding information is transmitted to an actuator, not shown, by electric conductors, not shown.

Figure 5:
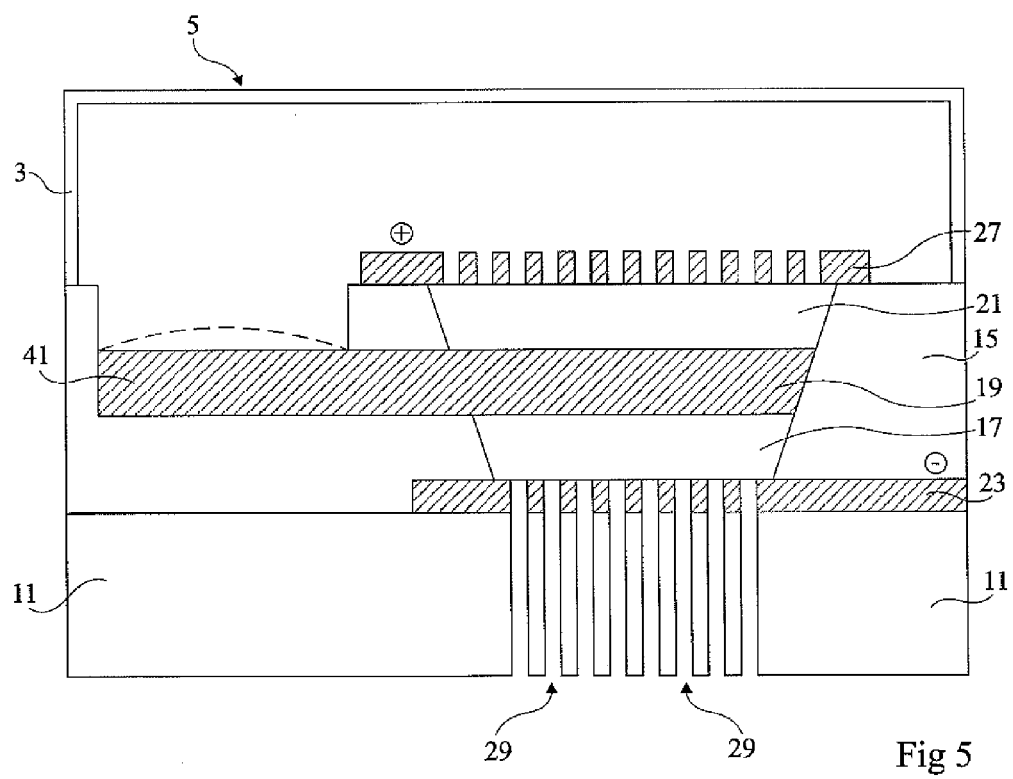

FIG. 5 illustrates a second embodiment of a device for controlling the humidity of a fuel cell.

The active portion of the fuel cell is identical to that of FIG. 4. Further, electrolyte 19 comprises an extension 41 in insulating layer 15 above which insulating layer 15 is opened. Extension 41 deforms according to the humidity ratio in the package, this deformation being shown in dotted lines in the drawing. The deformation may be detected by any appropriate means, for example, by a switch similar to switch 39 of FIG. 4. The detection of the deformation of an extension of the electrolyte enables to detect the humidity ratio as closely as possible thereto and thus to improve the detection.

Figure 6:
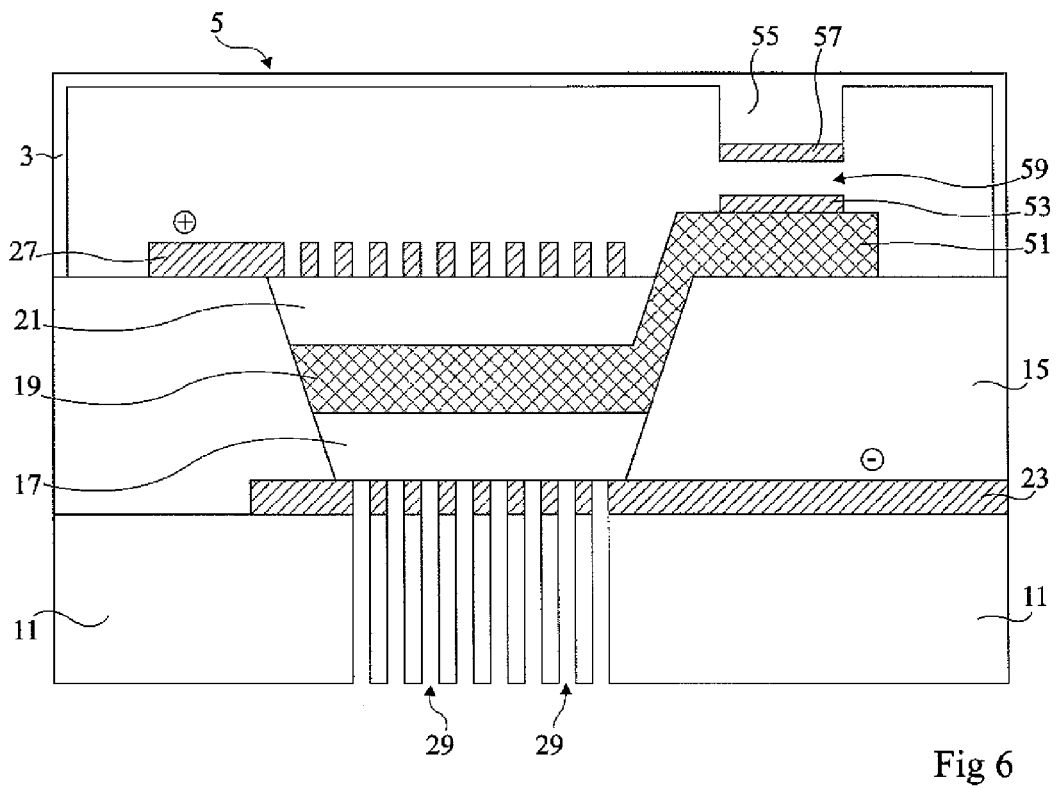

FIG. 6 illustrates a third embodiment of a device for controlling the humidity of a fuel cell.

In FIG. 6, a switch of detection of the humidity ratio in the package is placed on an extension 51 of the electrolyte which extends on insulating layer 15. A first metal terminal 53 extends on extension 51 and a vertical extension 55 of the upper portion of the package supports a second metal terminal 57, opposite to first terminal 53. Terminals 53 and 57 form a switch 59 which closes in association with the deformation of the material of extension 51. As in the embodiment of FIG. 5, the forming of switch 59 directly on an extension of the electrolyte enables detection of the humidity ratio at closest thereto.

The embodiment of FIG. 6 has the advantage of being relatively simple to form. Indeed, fuel-cell-forming methods generally provide forming an opening in insulating layer 15, then filling this opening with the active elements of the cell (catalyst layer 17, electrolyte layer 19, and catalyst layer 21). Electrolyte layer 19 is generally formed by coating, that is, by depositing a layer of a material in this opening and by appropriately spreading this malleable layer. Thus, to form extension 51, it is sufficient to spread the material of the electrolyte on a larger surface area and to cover a portion of insulating layer 15.

Figure 7:
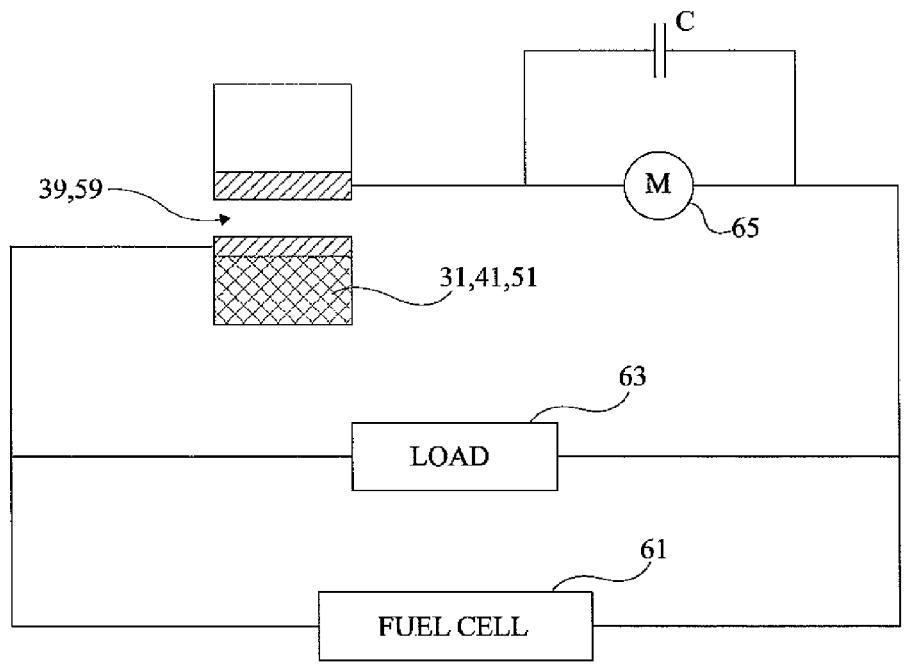
FIG. 7 is an electric diagram of a humidity control device.

FIG. 7 is an electric diagram of a fuel cell humidity control device.

A fuel cell 61 connected to a load 63 has been shown. A circuit comprising, in series, switches 39 or 59 and a motor 65 (M) is also connected across cell 61. Thus, when switch 39 or 59 is closed, the fuel cell powers motor 65. The motor is associated with the system for opening and closing mobile cap 5 of the fuel cell package. Thus, the power supply of the motor enables the opening of the mobile cap. When the mobile cap is open, the motor has a high impedance and thus become equivalent to an open switch. For example, a step-by-step motor controlled by a specialized integrated circuit enabling to set the outputs at high impedance, for example, the circuit known under reference number MC3479C.

A capacitor C is placed in parallel with motor 65. Thus, when switch 39 or 59 is closed, motor 65 is powered and capacitor C charges. If switch 39 or 59 opens (decrease of the humidity ratio in the package), the capacitor and the motor are then connected in closed circuit and the capacitor discharges into the motor. This enables, with an adapted motor, the closing of the mobile cap. Thus, the circuit of FIG. 7 enables to manage the humidity ratio in the package and thus to start the fuel cell several times.

It should be noted that a circuit without capacitor C may also be provided in the case where an initially-closed package which is desired to be definitively opened after a first starting of the fuel cell is provided. This may be useful in the case of devices likely to be stored for a long period before a regular use.

Figure 8:
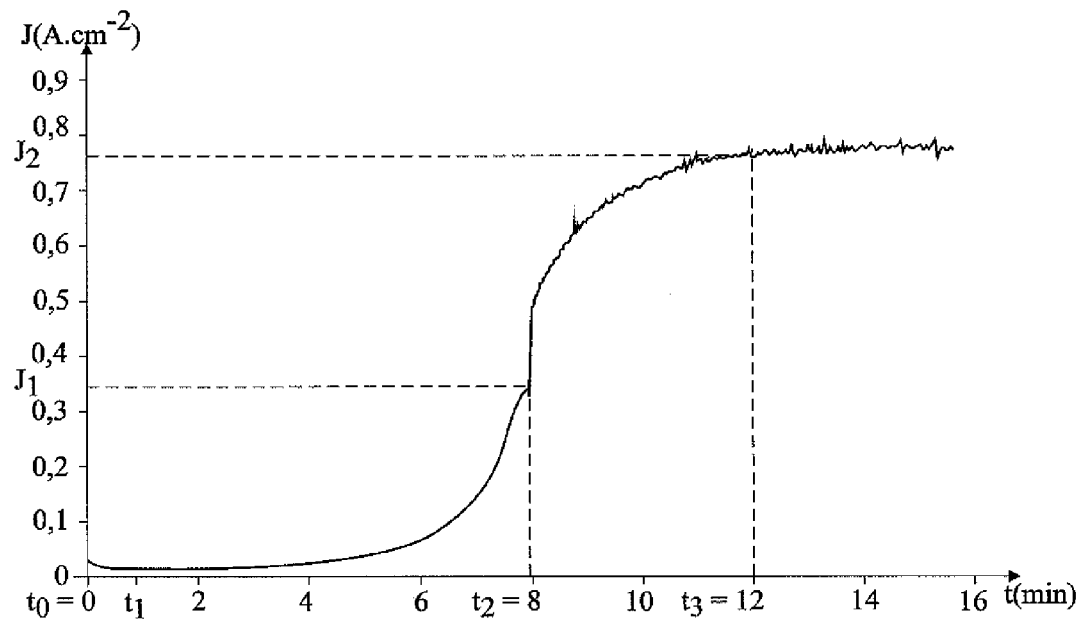
FIG. 8 is a curve illustrating the starting of a humidity-control fuel cell having its electrolyte in an initial dried-out state.

FIG. 8 is a curve illustrating the variation of the current density along time at the starting of a humidity-control fuel cell such as discussed hereabove, having its electrolyte in an initially dried-out state. The units are, as an example, minutes for abscissas and A.cm−2 for ordinates.

It is started from an initial state, at a time t0, in which the electrolyte of the fuel cell is in a dried-out state and in which cap 5 of the cell package is closed. Between time t0 and a time t1, the current supplied by the cell slightly decreases. Between time t1 and a time t2, the current supplied by the cell stagnates, then increases more and more to reach, at time t=t2, a value J1. This increase results from the evaporation of the water generated by the cell in the closed package and thus from the increase of the humidity ratio of the electrolyte. At a time t2, the switch associated with detector 7 closes, which powers motor 65 and causes the opening of mobile cap 5. The fuel cell keeps on delivering a current which increases, then reaches a state of equilibrium. At a time t3, the current density supplied by the cell reaches a nominal value J2.

Figure 9:
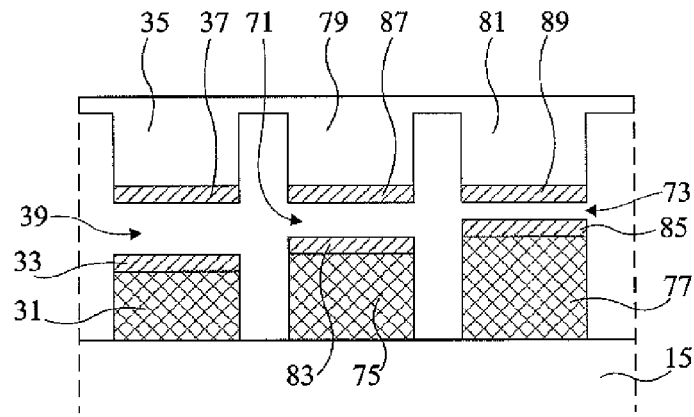
FIG. 9 illustrates an alternative embodiment of a humidity control device.

FIG. 9 illustrates a partial view of a variation of the humidity control device of FIG. 4 in which several switches are provided in the fuel cell package. In FIG. 9, only the right-hand upper portion of a device similar to that of FIG. 4, that is, the top of insulating layer 15 on which switch 39 is formed, has been shown.

Two other switches 71 and 73 are placed on insulating material layer 15, next to switch 39, and the information corresponding to these switches is transmitted to an actuator, not shown, by electric conductors, not shown. These switches respectively comprise pads 75 and 77 of a material deforming along with the humidity ratios, which extend on layer 15 and, opposite to pads 75 and 77, vertical extensions 79 and 81 of the upper portion of the package. First metallization terminals 83 and 85 extend on pads 75 and 77 and, second metal terminals 87 and 89 extend on vertical extensions 79 and 81. Pads 31, 75, and 77 have different thicknesses (thickness of pad 75 smaller than that of pad 77 and greater than that of pad 31). When the humidity increases in the package, switch 39 closes first. Switches 71 and 73 then successively close when the humidity ratio increases. Thus, according to the opening and to the closing of the different switches, different humidity ratios can be detected in the package. This enables, with an adapted electric circuit, to modify the opening of the mobile cap according to several positions as a function of the humidity ratio in the package and to control this humidity ratio for an optimal cell operation.

Pads 31, 75, and 77 of identical thicknesses but formed of different materials, having thicknesses varying faster or slower along with the humidity ratio, may also be provided. It should be understood that several switches may also be formed in parallel on extension 51 in the case of the embodiment of FIG. 6.

Figure 10:
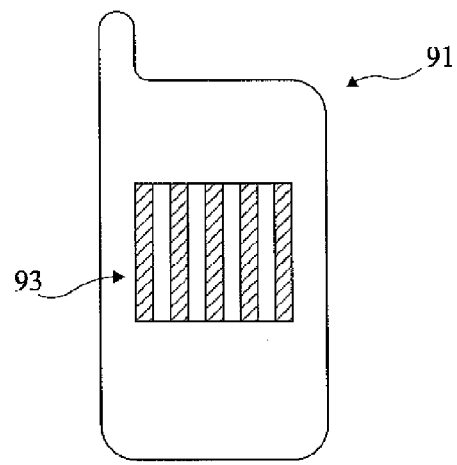
FIG. 10 illustrates an example of a cell phone powered by one or several fuel cells provided with humidity control devices.

FIG. 10 illustrates an example of the rear surface of a cell phone 91 comprising one or several fuel cells such as described herein. The package of the fuel cell(s) comprises an open mobile cap 93 on the outside of the phone. In the shown example, the mobile cap comprises sliding grids which enable its opening or closing, on the air supply side of the fuel cell(s).

It could also be provided to use a package comprising a mobile cap associated with other type of detectors of the humidity ratio in the fuel cell package. For example, the detector may be a device for measuring the resistance of the electrolyte, this resistance being directly linked to the humidity ratio of the electrolyte. A mobile cap comprising a large number of positions, according to this resistance, may be provided.

Specific embodiments of the present invention have been described. Various alterations and modifications will occur to those skilled in the art. In particular, other types of known fuel cells may be provided in a package comprising a controlled-opening mobile cap. The forming of the mobile cap has not been detailed, since many devices may be used to open and close the package of the fuel cell(s), on their oxygen-supply side.

The package comprising a mobile cap may be the package of one or of several fuel cells. It should be understood that several fuel cell packages may be topped with a same mobile cap or that several mobile caps may be controlled by a same actuator.

The detectors disclosed herein all comprise pads or extensions made of materials which expand according to the humidity ratio in the package. It should be noted that it may also be provided to use detectors comprising portions made of materials which shrink as the humidity ratio increases, in association with adapted electric circuits.

Further, the actuator has been described as being a motor. It may also be provided to use other types of actuators, for example, jacks.

Such alterations, modifications, and improvements are intended to be part of this disclosure, and are intended to be within the spirit and the scope of the present invention. Accordingly, the foregoing description is by way of example only and is not intended to be limiting. The present invention is limited only as defined in the following claims and the equivalents thereto.

What is claimed is:

1. An oxygen/hydrogen fuel cell comprising:
   a package comprising, on the side of the cell intended to be exposed to air, an enclosure provided with a mobile cap;
   an element made of a material that deforms according to a humidity ratio in the package;
   control means for controlling opening and the closing of the mobile cap; and
   a switch that opens and closes according to deformation of said element, said switch comprising two conductive terminals, a first conductive terminal of the two conductive terminals being arranged on a surface of said element made of the material that deforms according to the humidity ratio, said switch being electrically connected in series to said control means such that electrical power produced by the oxygen/hydrogen fuel cell is supplied to said control means via the switch when the switch is closed.

2. The fuel cell of claim 1, further comprising a layer forming an electrolyte of the oxygen/hydrogen fuel cell, the layer comprising the material deforming according to the humidity ratio.

3. The fuel cell of claim 1, wherein the control means comprise a motor.

4. The fuel cell of claim 3, wherein a capacitor is connected in parallel on the motor.

5. The fuel cell of claim 1, further comprising:
 a second element made of the material that deforms according to the humidity ratio in the package; and
 a second switch that opens and closes according to deformation of said second element, said second switch being electrically connected in series to said control means such that electrical power produced by the oxygen/hydrogen fuel cell is supplied to said control means via the second switch when the second switch is closed.

6. A cell phone comprising: the fuel cell of claim 1.

7. The fuel cell of claim 1, wherein:
the material that deforms according to the humidity ratio is a first material; and
the fuel cell further comprises:
 a second element made of a second material that deforms according to the humidity ratio in the package, the second material deforming according to the humidity ratio differently from the first material; and
 a second switch that opens and closes according to deformation of said second element, said second switch being electrically connected in series to said control means such that electrical power produced by the oxygen/hydrogen fuel cell is supplied to said control means via the second switch when the second switch is closed.

* * * * *